United States Patent
Bohner et al.

(10) Patent No.: US 7,226,527 B2
(45) Date of Patent: Jun. 5, 2007

(54) METHOD FOR RECOVERING CRUDE 1,3-BUTADIENE BY EXTRACTIVE DISTILLATION FROM A C$_4$ CUT

(75) Inventors: Gerd Bohner, Malsch (DE); Klaus Kindler, Harthausen (DE); Melanie Pahl, Mannheim (DE); Gerd Kaibel, Lampertheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 343 days.

(21) Appl. No.: 10/467,626

(22) PCT Filed: Feb. 6, 2002

(86) PCT No.: PCT/EP02/01219

§ 371 (c)(1),
(2), (4) Date: Aug. 8, 2003

(87) PCT Pub. No.: WO02/062733

PCT Pub. Date: Aug. 15, 2002

(65) Prior Publication Data
US 2004/0065538 A1    Apr. 8, 2004

(30) Foreign Application Priority Data
Feb. 8, 2001  (DE) ................ 101 05 660

(51) Int. Cl.
*B01D 3/40*    (2006.01)
*B01D 3/42*    (2006.01)
*C07C 7/08*    (2006.01)
*C07C 11/167*  (2006.01)

(52) U.S. Cl. .............. 203/2; 203/43; 203/50; 203/98; 203/DIG. 9; 585/810; 585/833; 585/615

(58) Field of Classification Search .......... 203/2, 203/43, 50, 98, DIG. 9; 202/158; 585/802, 585/810, 833, 615
See application file for complete search history.

(56) References Cited

U.S. PATENT DOCUMENTS

| 4,162,198 | A  | * | 7/1979 | Stockburger et al. ...... 203/23 |
| 4,292,141 | A  | * | 9/1981 | Lindner et al. ........... 203/49 |
| 6,348,637 | B1 | * | 2/2002 | Harris ................... 585/820 |
| 6,395,950 | B1 | * | 5/2002 | Rice ..................... 585/738 |
| 6,395,951 | B1 | * | 5/2002 | Hamm .................... 585/827 |

FOREIGN PATENT DOCUMENTS

| DE | 27 24 365  | 11/1978 |
| DE | 100 22 465 | 11/2001 |

* cited by examiner

*Primary Examiner*—Virginia Manoharan
(74) *Attorney, Agent, or Firm*—Oblon, Spivak, McClelland, Maier & Neustadt, P.C.

(57) ABSTRACT

A process for recovering crude 1,3-butadiene from a C$_4$ fraction by extractive distillation using a selective solvent in a dividing wall column (TK) in which a dividing wall (T) is arranged in the longitudinal direction of the column to form a first subregion (A), a second subregion (B) and a lower common column region (C) and which is preceded by an extractive scrubbing column (K) is proposed.

14 Claims, 2 Drawing Sheets

Figure 1:
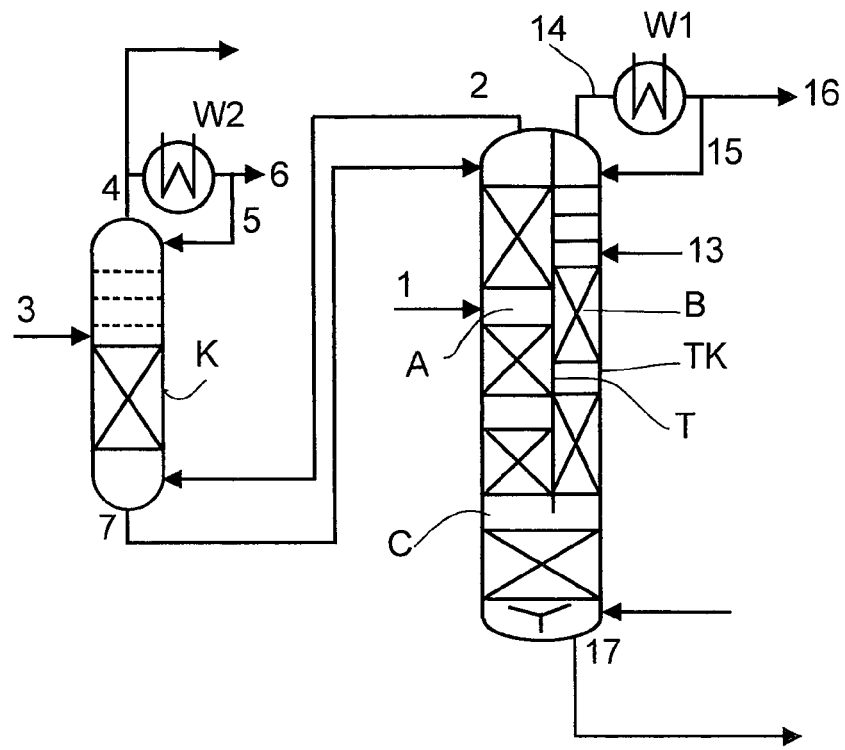

METHOD FOR RECOVERING CRUDE 1,3-BUTADIENE BY EXTRACTIVE DISTILLATION FROM A C₄ CUT

The present invention relates to a process for recovering crude 1,3-butadiene from a $C_4$ fraction by extractive distillation using a selective solvent and a apparatus suitable for this purpose.

The recovery of crude 1,3-butadiene from a $C_4$ fraction is a complicated distillation problem because of the small differences in the relative volatility of the components of the $C_4$ fraction. The fractionation is therefore carried out by means of an extractive distillation, i.e. a distillation with addition of an extractant which has a boiling point higher than that of the mixture to be fractionated and increases the differences in the relative volatility of the components to be separated. Use of suitable extractants enables the abovementioned $C_4$ fraction to be fractionated by means of extractive distillation to give a crude 1,3-butadiene fraction which is subsequently purified further in pure distillation columns together with a stream comprising the hydrocarbons which are less soluble than 1,3-butadiene, in particular butanes and butenes, and a stream comprising the hydrocarbons which are more readily soluble than 1,3-butadiene, in particular the butynes and possibly 1,2-butadiene.

For the purposes of the present invention, crude 1,3-butadiene is a hydrocarbon mixture comprising at least 80% by weight, preferably 90% by weight, particularly preferably 95% by weight, of 1,3-butadiene as product of value, with the balance being impurities.

On the other hand, the term pure 1,3-butadiene is used to refer to a hydrocarbon mixture comprising at least 99% by weight, preferably 99.5% by weight, particularly preferably 99.7% by weight, of 1,3-butadiene as product of value, with the balance being impurities.

DE-A 27 24 365 describes a process for recovering 1,3-butadiene from a $C_4$ fraction in which a crude 1,3-butadiene is initially obtained by extractive distillation and is subsequently processed further by distillation to give pure 1,3-butadiene.

In the process of DE-A 27 24 365, the extractive distillation is carried out in a plant comprising three columns, the main scrubber, countercurrent column and after-scrubber. In the main scrubber, the vaporized $C_4$ fraction is brought into countercurrent contact with the extractant, in particular N-methylpyrrolidone, hereinafter referred to as NMP for short.

Here, the components which are relatively readily soluble in NMP, viz. propyne, butenyne, 1-butyne, 1,2-butadiene, 1,3-butadiene and cis-2-butene, are absorbed in NMP. The components which are less readily soluble in NMP than 1,3-butadiene, in particular a mixture of butenes and butanes, are taken off at the top of the main scrubber. The bottom product of the main scrubber is pumped to the top of the second column of the extractive distillation plant, viz. the countercurrent column. The countercurrent column consists of an upper section and a lower section which have different functions: the upper part represents, in engineering terms, the extension of the main scrubber, while the lower part acts like the after-scrubber. In the upper part, the residual butenes dissolved in the solvent are stripped out and fed back to the main scrubber. At the transition from the lower part to the upper part of the countercurrent column, a stream which is enriched in 1,3-butadiene and additionally contains components which are more soluble than 1,3-butadiene, in particular $C_3$- and $C_4$-acetylenes together with 1,2-butadiene, cis-2-butene and $C_5$-hydrocarbons, is taken off. Since part of the ascending vapor is thus taken off at the transition from the lower part to the upper part of the countercurrent column, the upper part of the countercurrent column has to have, for hydrodynamic reasons, a smaller diameter than the lower part to ensure sufficiently good mass transfer in the overall column. The taper required for this is more difficult to realize in constructional terms than an apparatus having a constant diameter over the entire height.

At the bottom of the countercurrent column, preliminary degassing of the hydrocarbons dissolved in NMP occurs; partially degassed NMP is pumped to the degasser column for complete degassing.

In a third column of the extractive distillation plant, viz. the after-scrubber, the $C_4$-acetylenes are removed from the gaseous 1,3-butadiene-containing stream taken off at the transition between upper part and lower part of the countercurrent column, likewise by selective countercurrent scrubbing with NMP. The components 1-butyne and butenyne which are more readily soluble in NMP than is 1,3-butadiene go into solution and the product obtained at the top of the after-scrubber is crude 1,3-butadiene, namely a hydrocarbon mixture having the above-defined minimum concentration of desired product 1,3-butadiene and additionally containing, as impurities, 1,2-butadiene, propyne, cis-2-butene and $C_5$-hydrocarbons.

The bottom product from the after-scrubber, viz. NMP laden with $C_4$-acetylene and 1,3-butadiene, is pumped back to the countercurrent column. The $C_4$-acetylenes are recovered in the bottom of the countercurrent column from where they are pumped together with the partially degassed NMP stream to the degasser column for complete degassing. The $C_4$-acetylenes are discharged from the system as a stream taken off at a side offtake on the degasser column and are discharged via a small water scrub to avoid solvent losses and also partial condensation using cooling water.

The work-up of the laden NMP is carried out by heating and preliminary degassing of the bottoms from the countercurrent column in the abovementioned degasser column in which completely degassed NMP is obtained at the bottom and a gaseous hydrocarbon stream is obtained at the top. The latter is returned via a compressor to the bottom region of the countercurrent column.

The process known from DE-A27 24 365 for recovering crude 1,3-butadiene from a $C_4$ fraction by extractive distillation has the particular disadvantage that it requires an extractive distillation plant comprising three columns, with the middle column, viz. the countercurrent column, having to be provided, for thermodynamic reasons, with a larger diameter in the lower part and a smaller diameter in the upper part and therefore a constructionally difficult narrowing between lower part and upper part.

It is an object of the present invention to provide an improved, in particular more economical, process for recovering crude 1,3-butadiene from a $C_4$ fraction by extractive distillation and to provide an extractive distillation apparatus suitable for this purpose.

We have found that this object is achieved by a process for recovering crude 1,3-butadiene from a $C_4$ fraction by extractive distillation using a selective solvent in a dividing wall column in which a dividing wall is arranged in the longitudinal direction of the column to form a first subregion, a second subregion and a lower common column region and an upstream extractive scrubbing column.

The invention thus provides a process for recovering crude 1,3-butadiene by extractive distillation and an extractive distillation plant suitable for this purpose, according to which only two columns which have a constant diameter over the entire column height and thus no narrowing are required.

The $C_4$ fraction to be used as starting mixture in the present process is a mixture of hydrocarbons having predominantly four carbon atoms per molecule. $C_4$ fractions are obtained, for example, in the preparation of ethylene and/or propylene by thermal cracking of a petroleum fraction such as liquefied petroleum gas, light naphtha or gas oil. Furthermore, $C_4$ fractions are obtained in the catalytic dehydrogenation of n-butane and/or n-butene. $C_4$ fractions generally comprise butanes, n-butene, isobutene, 1,3-butadiene and small amounts of $C_3$- and $C_5$-hydrocarbons, and also butynes, in particular 1-butyne (ethylacetylene) and butenyne (vinylacetylene). The 1,3-butadiene content is generally from 10 to 80% by weight, preferably from 20 to 70% by weight, in particular from 30 to 60% by weight, while the content of vinylacetylene and ethylacetylene generally does not exceed 5% by weight.

A typical $C_4$ fraction has the following composition in percent by weight:

| | |
|---|---|
| Propane | 0–0.5 |
| Propene | 0–0.5 |
| Propadiene | 0–0.5 |
| Propyne | 0–0.5 |
| n-butane | 3–10 |
| i-butane | 1–3 |
| 1-butene | 10–20 |
| i-butene | 10–30 |
| trans-2-butene | 2–8 |
| cis-2-butene | 2–6 |
| 1,3-butadiene | 30–60 |
| 1,2-butadiene | 0.1–1 |
| ethylacetylene | 0.1–2 |
| vinylacetylene | 0.1–3 |
| $C_5$-hydrocarbons | 0–0.5 |

For the present separation problem, namely the recovery of 1,3-butadiene from the $C_4$ fraction, possible extractants, i.e. selective solvents, for the extractive distillation defined at the outset are substances or mixtures in general which have a boiling point higher than that of the mixture to be fractionated and have a greater affinity to conjugated double bonds and triple bonds than to simple double bonds or single bonds, preferably dipolar solvents, particularly preferably dipolar aprotic solvents. Substances which are noncorrosive or have little corrosivity are preferred so as to avoid corrosion of the apparatus.

Selective solvents which are suitable for the process of the present invention are, for example, butyrolactone, nitriles such as acetonitrile, propionitrile, methoxypropionitrile, ketones such as acetone, furfural, N-alkyl-substituted lower aliphatic acid amides such as dimethylformamide, diethylformamide, dimethylacetamide, diethylacetamide, N-formylmorpholine, N-alkyl-substituted cyclic acid amines (lactams) such as N-alkylpyrrolidones, in particular N-methylpyrrolidone. In general, use is made of N-alkyl-substituted lower aliphatic acid amides or N-alkyl-substituted cyclic acid amides. Particularly advantageous extractants are dimethylformamide and, in particular, N-methylpyrrolidone.

It is also possible to use mixtures of these solvents with one another, for example of N-methylpyrrolidone with acetonitrile, mixtures of these solvents with cosolvents such as water and/or tert-butyl ethers, for example methyl tert-butyl ether, ethyl tert-butyl ether, propyl tert-butyl ether, n-butyl tert-butyl ether or isobutyl tert-butyl ether.

A particularly useful extractant is N-methylpyrrolidone, in the present text referred to as NMP for short, preferably in aqueous solution, in particular containing from 7 to 10% by weight of water, particularly preferably containing 8.3% by weight of water.

According to the present invention, the process is carried out in a dividing wall column in which a dividing wall is arranged in the longitudinal direction of the column to form a first subregion, a second subregion and a lower common column region and which is connected to an upstream extractive scrubbing column.

Dividing wall columns are, as is known, used for relatively complex separation tasks, in general for mixtures of at least three components which are each to be obtained in pure form. They have a dividing wall, i.e. generally a flat metal sheet aligned in the longitudinal direction of the column, which prevents transverse mixing of the liquid and vapor streams in subregions of the column.

For the purposes of the present invention, use is made of a dividing wall column having a particular configuration, whose dividing wall continues to the uppermost point of the column and thus allows mixing of liquid and vapor streams only in the lower common column region. The first and second subregions are separated from one another by the dividing wall.

The extractive scrubbing column is a countercurrent scrubbing column and corresponds essentially to the main scrubber known from the prior art. However, for a capacity comparable to that of the plant known from the prior art, the extractive scrubbing column is not as high as the main scrubber since part of the separation task of the main scrubber is now taken over by the upper region of the first subregion of the dividing wall column.

In a preferred way of carrying out the process,
the $C_4$ fraction is fed to the first subregion, preferably in its middle region,
the stream taken off at the top from the first subregion of the dividing wall column is fed to the extractive scrubbing column in its lower region,
a countercurrent extraction is carried out in the extractive scrubbing column by treatment with a first substream of the selective solvent in the upper region of the extractive scrubbing column,
the components of the $C_4$ fraction which are less soluble that 1,3-butadiene in the selective solvent are taken off at the top of the extractive scrubbing column,
the bottom stream from the extractive scrubbing column is recirculated to the upper region of the first subregion of the dividing wall column,
a second substream of the selective solvent is fed to the dividing wall column in the middle region of the second subregion,
selective solvent laden with 1,3-butadiene together with components of the $C_4$ fraction which are more soluble than 1,3-butadiene in the selective solvent is taken off from the bottom of the dividing wall column and
the product is taken off at the top from the second subregion of the dividing wall column as crude 1,3-butadiene.

It is thus preferred that the $C_4$ fraction to be fractionated is fed to the first subregion of the dividing wall column, particularly preferably in its middle region;
the stream from the top of the first subregion of the dividing wall column is recirculated to the upstream extractive scrubbing column in its lower region, a countercurrent extraction is carried out in the extractive scrubbing column by treatment with a first substream of the selective solvent in the upper region of the extractive scrubbing column, the components of the $C_4$ fraction which are less soluble than 1,3-butadiene in the selective solvent are taken off at the top of the extractive scrubbing column, particularly preferably condensed in a condenser at the top of the extractive scrubbing column and partly returned as runback to the extractive scrubbing column while the remainder is taken off as a predominantly butane- and butene-containing by-product.

As a result of the recirculation of the stream from the bottom of the extractive scrubbing column, i.e. a stream comprising the selective solvent, 1,3-butadiene and the components of the $C_4$ fraction which are more soluble than 1,3-butadiene in the selective solvent, into the upper region of the first subregion of the dividing wall column and mass transfer between the stream and the $C_4$ fraction introduced in vapor form in the upper region of the first subregion of the dividing wall column, countercurrent extraction can take place with discharge of the components which are less soluble than 1,3-butadiene in the selective solvent at the top of the first subregion of the dividing wall column.

At the lower end of the dividing wall, a gaseous stream comprising 1,3-butadiene together with the components of the $C_4$ fraction which are more soluble than 1,3-butadiene in the selective solvent, in particular $C_4$-acetylenes, is obtained. These are scrubbed in countercurrent from the ascending gaseous stream by means of a second substream of the selective solvent which is introduced into the middle region of the second subregion of the dividing wall column. The gaseous product from the top of the second subregion of the dividing wall column is taken off and preferably condensed in a condenser at the top of the column, a substream of the condensed top stream is returned as runback to the subregion B of the dividing wall column and the remainder of the condensed top stream is taken off as crude 1,3-butadiene.

The lower common column region of the dividing wall column corresponds in process engineering terms to the lower part of the countercurrent column of the extractive distillation plant known from the prior art. In this common column region, as in the corresponding apparatus section from the known processes, preliminary degassing of the hydrocarbons dissolved in the selective solvent, their recirculation into the first subregion of the dividing wall column corresponding to the extension of the main scrubber and the taking-off of the partially laden solvent from the bottom of the column to the degasser column for the purpose of complete degassing take place.

In a preferred process variant, the vapor stream at the lower end of the dividing wall of the dividing wall column is divided by means of suitable measures so that the substream conveyed to the first subregion of the dividing wall column is larger than the substream conveyed to the second subregion of the dividing wall column. Regulation of the division of the stream of vapor at the lower end of the dividing wall enables the necessary product specification of the crude 1,3-butadiene stream taken off at the top of the second subregion of the dividing wall column to be ensured in a simple and reliable manner.

Such unequal division of the stream vapor at the lower end of the dividing wall is particularly preferably achieved by the dividing wall being arranged noncentrally so that the second subregion is smaller than the first subregion of the dividing wall column.

The dividing wall is particularly preferably arranged noncentrally so that the cross-sectional ratio of the first subregion to the second su 1.5:1, in particular 2.3:1.

As an alternative to or in addition to the noncentral arrangement of the dividing wall, the stream of vapor at the lower end of the dividing wall can be divided in the desired ratio between the two subregions of the dividing wall column by means of further measures, for example flaps or guide plates.

A further additional or alternative measure for division of the stream of vapor at the lower end of the dividing wall is setting of the heat removal power of the condenser at the top of the second subregion of the dividing wall column.

In a preferred process variant, the pressures at the upper end of the two subregions of the dividing wall column can each be regulated separately. This enables the necessary product specification of the crude 1,3-butadiene to be ensured.

The pressures at the top of the two subregions of the dividing wall column are preferably each set by means of a split-range control. The term split-range control refers, in a well-known manner, to an arrangement in which the outlet of the pressure regulator is connected simultaneously to the inert gas line and the venting line. The valve setting range of the pressure regulator is divided so that only one valve is actuated at one time, i.e. either inert gas flows in or venting occurs. This enables the amount of inert gas and the product losses associated with the waste air stream to be minimized.

In addition to or as an alternative to split-range control, it is possible to regulate each of the pressures at the top of the two subregions of the dividing wall column by means of the heat removal power of the condensers at the top of the second subregion of the dividing wall column and at the top of the extractive scrubbing column.

In a preferred process variant, the pressure at the top of the second subregion of the dividing wall column is set so as to be greater than that in the first region of the dividing wall column, in particular by 1–100 mbar, particularly preferably by 1–30 mbar. This measure makes it possible to dispense with a fixed, welded-in or expensively sealed dividing wall and to use a cheaper removable dividing wall. The pressure drop from the second to the first subregion of the dividing wall column allows liquid or gaseous leakage flows to occur only in this direction, so that they are not critical for the purity of the desired crude 1,3-butadiene taken off at the top of the second subregion.

The pressure at the top of the second subregion of the dividing wall column is preferably set to a value in the range 3–7 bar absolute, in particular 4–6 bar absolute. This makes it possible to carry out the condensation at the top of the dividing wall column by means of water as coolant without having to use more expensive coolants.

The invention also provides an apparatus for carrying out the process for recovering crude 1,3-butadiene from a $C_4$ fraction by extractive distillation using a selective solvent, which comprises a dividing wall column in which a dividing wall is arranged in the longitudinal direction of the column to form a first subregion, a second subregion and a lower common column region, and also an upstream extractive scrubbing column.

In a preferred embodiment, the dividing wall column contains random packing elements or ordered packing as separation-active internals in all regions of the column except for the region above the inlet for the second solvent substream in the second subregion which is provided with trays. As an alternative or in addition, the upstream extractive scrubbing column contains trays as separation-active internals above the inlet for the first solvent substream and contains random packing elements or ordered packing below the inlet for the first solvent substream.

The upper region of the second subregion of the dividing wall column, above the inlet for the second solvent substream, has to be provided with trays because of the low liquid throughput. The same applies to the upper subregion of the extractive scrubbing column above the inlet for the first solvent substream.

Otherwise, both the dividing wall column and the extractive scrubbing column are provided in other regions with random packing elements or ordered packing as preferred separation-active devices.

Owing to the relatively high proportion of components having a high tendency to polymerize and thus an increased risk of fouling in the equipment items in each of the lower regions of the two subregions of the dividing wall column, coarser random packing elements or ordered packing are preferably used there compared to the upper regions of the subregions of the dividing wall column.

Particular preference is given to an apparatus comprising a dividing wall column which is equipped with a bed of random packing elements having 23 theoretical plates in the first subregion below the inlet for the $C_4$ fraction and with a bed of random packing elements having 12 theoretical plates above the inlet for the $C_4$ fraction, with 6 practical trays in the second subregion above the inlet for the second solvent substream and with a bed of random packing elements having 30 theoretical plates below the inlet for the second solvent substream and with a bed of random packing elements having 7 theoretical plates in the lower common column region, and/or comprising an extractive scrubbing column which is equipped with 6 practical trays in its upper region above the inlet for the second solvent substream and with a bed of random packing elements having 15 theoretical plates located underneath.

The invention thus provides an apparatus for recovering crude 1,3-butadiene from a $C_4$ fraction by extractive distillation which requires only two compared to the previous three columns of known apparatuses. Furthermore, these two columns have a constant diameter over their entire height. As a result, the capital costs are about 10% lower than for an apparatus of the prior art having the same capacity.

Figure 1A:
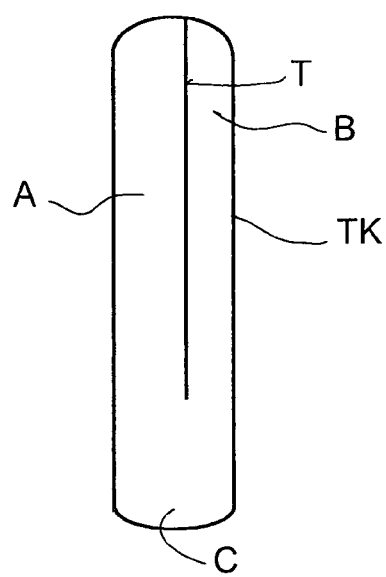
Figure 2:
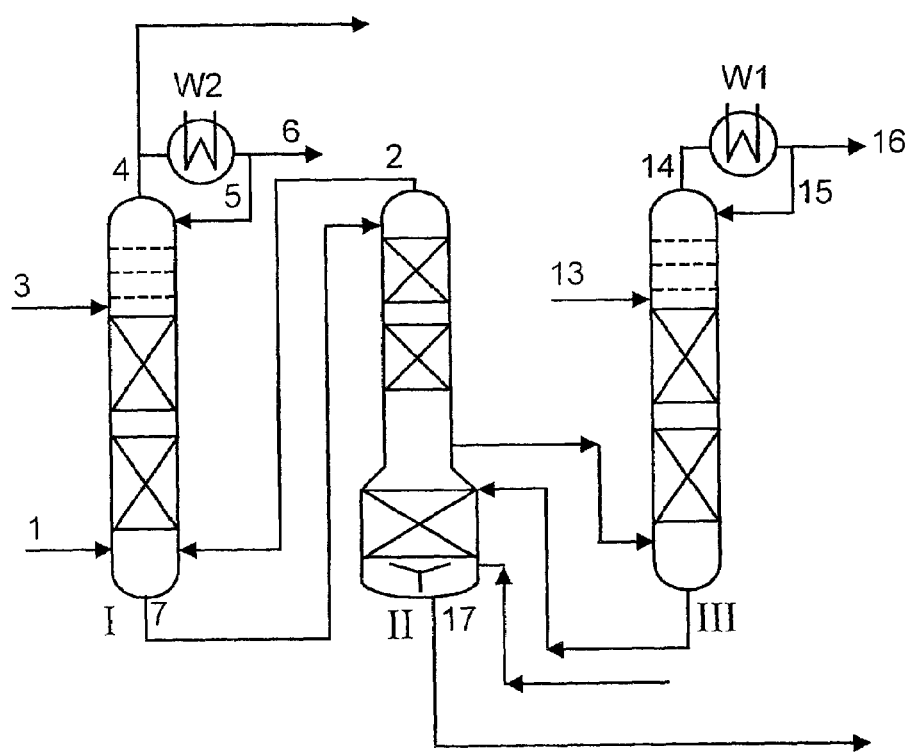

The invention is illustrated below with the aid of a drawing:

FIG. 1 shows a flow diagram of an apparatus according to the invention, with the arrangement of the dividing wall in the dividing wall column being shown schematically in FIG. 1*a*, FIG. 2 shows a flow diagram of an apparatus according to the prior art.

FIG. 1 schematically shows an apparatus according to the invention. In a dividing wall column TK having a dividing wall T which is arranged in the longitudinal direction of the column and divides the dividing wall column into a first subregion A, a second subregion B and a lower common column region C, a $C_4$ fraction 1 is fed into the first subregion A. The stream 2 from the top of the subregion A is conveyed to the lower region of the upstream extractive scrubbing column K. A first solvent substream 3 is introduced into the upper region of the extractive scrubbing column K, so that countercurrent extraction takes place and gives a bottom stream 7 which is returned to the upper region of the subregion A of the dividing wall column TK and a top stream 4 which is condensed in a condenser W2 at the top of the extractive scrubbing column K, with a substream of the condensate being returned as stream 5 to the extractive scrubbing column K and the remainder being taken off as stream 6.

A second solvent substream 13 is introduced into the second subregion B of the dividing wall column TK. A stream 17 which has been partly degassed in the lower common column region C is taken off at the bottom of the dividing wall column and a top stream 14 is taken off from the second subregion B sand condensed in the condenser W1, with a substream 15 being returned as runback to the second subregion B of the dividing wall column and the remainder being taken off as crude 1,3-butadiene (stream 16).

The schematic depiction in FIG. 1*a* serves to clarify the arrangement of the dividing wall T in the dividing wall column TK and the subregions formed in this way in the dividing wall column TK: the dividing wall T, which is arranged in the longitudinal direction of the dividing wall column TK, divides the latter into a first subregion, a second subregion B and a lower common column region C.

For comparison, FIG. 2 shows a flow diagram of an apparatus according to the prior art. Here, streams corresponding to those in FIG. 1 are each denoted by the same reference numerals. The three columns forming the extractive distillation apparatus have been denoted by the reference numerals I to III.

We claim:

1. A process for recovering crude 1,3-butadiene from a $C_4$ fraction by extractive distillation using a selective solvent, which is carried out in a dividing wall column in which a dividing wall is arranged in the longitudinal direction of the column to form a first subregion, a second subregion and a lower common column region and which is preceded by an extractive scrubbing column, wherein the $C_4$ fraction (1) is fed to the first subregion a stream taken off at the top from the first subregion of the dividing wall column is fed to the extractive scrubbing column in its upper region, a countercurrent extraction is carried out in the extractive scrubbing column by treatment with a first substream of the selective solvent in the upper region of the extractive scrubbing column, the components of the $C_4$ fraction which are less soluble than 1,3-butadiene in the selective solvent are taken off at the top of the extractive scrubbing column, a bottom stream from the extractive scrubbing column is recirculated to the upper region of the first subregion of the dividing wall column, a second substream of the selective solvent is fed to the dividing wall column in the middle region of the second subregion, selective solvent laden with 1,3-butadiene together with components of the $C_4$ fraction which are more soluble than 1,3-butadiene in the selective solvent is taken off from the bottom of the dividing wall column, and the product is taken off at the top from the second subregion of the dividing wall column as crude 1,3-butadiene.

2. A process as claimed in claim 1, wherein the components of the $C_4$ fraction which are less soluble than 1,3-butadiene in the selective solvent are taken off at the top of the extractive scrubbing column and condensed in a condenser, a substream of the condensate is returned as runback to the extractive scrubbing column and the remainder of the condensate is discharged, and/or the product taken off at the top from the second subregion of the dividing wall column is condensed in a condenser at the top of the dividing wall column, a substream of the condensed top product is returned to the subregion of the dividing wall column and the remainder of the condensed top stream is taken off as crude 1,3-butadiene.

3. A process as claimed in claim 1, wherein a stream of vapor is divided at the lower end of the dividing wall of the dividing wall column by means of suitable measures so that a substream conveyed into the first subregion of the dividing wall column is larger than a substream conveyed into the second subregion of the dividing wall column.

4. A process as claimed in claim 1 carried out in a dividing wall column having a noncentrally arranged dividing wall.

5. A process as claimed in claim 4, wherein, due to the noncentral arrangement of the dividing wall, the cross-sectional ratio of the first subregion to the second subregion is in the range from 8:1 to 1.5:1.

6. A process as claimed in claim 3, wherein the division of the stream of vapor at the lower end of the dividing wall is carried out by setting the heat removal power of a condenser at the top of the second subregion of the dividing wall column.

7. A process as claimed in claim 1, wherein the pressures at the upper end of the first and second subregions can each be regulated separately.

8. A process as claimed in claim 7, wherein the pressures at the top of the first and second subregions of the dividing wall column are each set via a split-range control.

9. A process as claimed in claim 1, wherein the pressures at the top of the first and second subregions of the dividing wall column are each regulated via the heat removal power of condensers.

10. A process as claimed in claim 1, wherein the pressure at the top of the second subregion of the dividing wall column is greater than the pressure at the top of the first subregion of the dividing wall column.

11. A process as claimed in claim 1, wherein the pressure at the top of the second subregion of the dividing wall column is set to a value in the range from 3 to 7 bar absolute.

12. A process as claimed in claim 1, wherein the dividing wall column contains random packing elements or ordered packing as separation-active internals in all regions of the column except for the region above an inlet for the second substream of the selective solvent in the second subregion which is provided with trays, and/or the upstream extractive scrubbing column contains trays as separation-active internals above an inlet for the first substream of the selective solvent and contains random packing elements or ordered packing below the inlet for the first solvent substream.

13. A process as claimed in claim 1, wherein coarser random packing elements or ordered packing are used in the lower common column region and in the lower regions of the first and second subregions of dividing wall column compared to upper regions of the first and second subregions of the dividing wall column.

14. A process as claimed in claim 1, wherein the dividing wall column is equipped with a bed of random packing elements having 23 theoretical plates in the first subregion below an inlet for the $C_4$ fraction and with a bed of random packing elements having 12 theoretical plates above the inlet for the $C_4$ fraction, with 6 practical trays in the second subregion above an inlet for the second substream of the selective solvent and the second substream of the selective solvent and with a bed of random packing elements having 7 theoretical plates in the lower common column region, and/or the extractive scrubbing column is equipped with 6 practical trays in its upper region above an inlet for the the first substream of the selective solvent and with a bed of random packing elements having 15 theoretical plates located underneath.

* * * * *